United States Patent
Hutchinson et al.

(10) Patent No.: US 11,505,442 B2
(45) Date of Patent: Nov. 22, 2022

(54) CONNECTOR

(71) Applicant: HEINEKEN UK LIMITED, Edinburgh (GB)

(72) Inventors: Guy Hutchinson, Twickenham (GB); Stuart Briant, Nottingham (GB); Simon Gray, Nottingham (GB)

(73) Assignee: Heineken UK Limited, Edinburgh (GB)

( * ) Notice: Subject to any disclaimer, the term of this patent is extended or adjusted under 35 U.S.C. 154(b) by 485 days.

(21) Appl. No.: 16/300,237

(22) PCT Filed: May 10, 2017

(86) PCT No.: PCT/GB2017/051287
§ 371 (c)(1),
(2) Date: Nov. 9, 2018

(87) PCT Pub. No.: WO2017/194929
PCT Pub. Date: Nov. 16, 2017

(65) Prior Publication Data
US 2019/0144254 A1    May 16, 2019

(30) Foreign Application Priority Data

May 11, 2016  (GB) ..................................... 1608280
Apr. 10, 2017  (GB) ..................................... 1705724

(51) Int. Cl.
*B67D 1/08* (2006.01)
*B67D 1/12* (2006.01)
*G01N 33/14* (2006.01)

(52) U.S. Cl.
CPC ......... *B67D 1/0841* (2013.01); *B67D 1/0829* (2013.01); *B67D 1/1247* (2013.01); *B67D 1/1272* (2013.01); *G01N 33/14* (2013.01)

(58) Field of Classification Search
CPC ......... G01N 27/22–221; G01N 27/226; G01N 33/14–146; B67D 1/1247; B67D 1/1422; B67D 1/1272
See application file for complete search history.

(56) References Cited

U.S. PATENT DOCUMENTS 3,635,082 A * 1/1972 Prellwitz ................. G01F 1/712
                                                73/861.04
3,878,970 A * 4/1975 Nezworski ........... B67D 1/1245
                                                222/61

(Continued)

FOREIGN PATENT DOCUMENTS

CN          203628006        6/2014
DE   10 2006 026 025 A1    12/2006

(Continued)

OTHER PUBLICATIONS

Search Report issued in GB 1608280.2 dated Nov. 14, 2016.

(Continued)

*Primary Examiner* — Paul R Durand
*Assistant Examiner* — Randall A Gruby
(74) *Attorney, Agent, or Firm* — Womble Bond Dickinson (US) LLP (57) ABSTRACT

The present invention provides a connector (18) for use in a beverage dispense system (1), the connector (18) defining a conduit for connecting a beverage line (2) to a beverage supply (4). The connector (18) comprises an electrical sensor (21) (e.g. a capacitive sensor) for measuring an electrical parameter of a beverage within the connector conduit. The electrical parameter and/or changes in the electrical parameter can be used to detect bubbles in the beverage and/or identify the type/brand of beverage.

20 Claims, 5 Drawing Sheets

(56) References Cited

U.S. PATENT DOCUMENTS

| | | | | |
|---|---|---|---|---|
| 3,898,637 A * | 8/1975 | Wolstenholme | ........... | F17D 3/01 340/606 |
| 4,406,382 A * | 9/1983 | Roth | ............ | B67D 1/1247 137/551 |
| 4,487,057 A * | 12/1984 | Lutz | ............ | G01K 3/00 174/11 R |
| 4,841,770 A * | 6/1989 | Davies | ............ | G01F 23/245 33/723 |
| 4,965,206 A * | 10/1990 | Kell | ............ | G01N 33/48735 435/287.1 |
| 5,035,139 A * | 7/1991 | Hoefelmayr | ............ | G01N 9/36 73/223 |
| 5,090,440 A * | 2/1992 | Ladouceur | ............ | B08B 9/0323 137/209 |
| 5,208,544 A * | 5/1993 | McBrearty | ............ | G01N 27/226 324/663 |
| 5,423,206 A * | 6/1995 | Hetzel | ............ | G01N 33/497 73/304 C |
| 5,636,763 A * | 6/1997 | Furness | ............ | B08B 9/0325 222/148 |
| 5,646,539 A * | 7/1997 | Godina | ............ | F15B 19/00 324/676 |
| 5,861,755 A * | 1/1999 | Moerk | ............ | G01F 1/74 324/663 |
| 5,935,433 A * | 8/1999 | Stefanini | ............ | B01J 19/12 210/222 |
| 6,299,020 B1 * | 10/2001 | Sudolcan | ............ | B67D 1/1243 222/1 |
| 6,545,488 B2 * | 4/2003 | Yamagishi | ............ | G01N 27/221 324/672 |
| 6,655,221 B1 * | 12/2003 | Aspelund | ............ | G01F 1/363 73/861.04 |
| 6,965,243 B2 * | 11/2005 | Yamagishi | ............ | G01N 27/226 324/658 |
| 7,036,687 B1 * | 5/2006 | Lowe | ............ | A47J 31/401 222/129.1 |
| 7,248,620 B2 * | 7/2007 | Bott | ............ | H03M 13/23 375/135 |
| 7,866,201 B1 * | 1/2011 | Tutu | ............ | G01N 27/22 73/19.05 |
| 8,297,131 B2 * | 10/2012 | Hughes | ............ | G01F 11/284 73/861.08 |
| 8,464,903 B2 * | 6/2013 | Baker | ............ | B67D 1/0867 222/1 |
| 10,464,799 B2 * | 11/2019 | Carson | ............ | B67D 1/07 |
| 2002/0088823 A1 * | 7/2002 | Tabacchi | ............ | B67D 1/1234 222/52 |
| 2003/0183249 A1 * | 10/2003 | Nissinen | ............ | B67D 1/1272 134/22.11 |
| 2003/0184317 A1 * | 10/2003 | Yamagishi | ............ | C12C 13/00 324/663 |
| 2006/0169715 A1 * | 8/2006 | Emmendorfer | ............ | B67D 1/07 222/59 |
| 2011/0309109 A1 * | 12/2011 | Paulitsch | ............ | F25D 31/002 222/146.6 |
| 2014/0263433 A1 * | 9/2014 | Merrifield | ............ | B67D 1/0867 222/66 |
| 2017/0233238 A1 * | 8/2017 | Bryant | ............ | F25B 13/00 62/126 |
| 2020/0393398 A1 * | 12/2020 | Smith | ............ | G01N 33/2847 |
| 2021/0238022 A1 * | 8/2021 | McDougall | ............ | B67D 1/1247 |

FOREIGN PATENT DOCUMENTS

| | | |
|---|---|---|
| GB | 2281554 | 3/1995 |
| GB | 2437174 | 10/2007 |
| GB | 2511851 A | 9/2014 |
| SK | 54-2012 | 4/2012 |
| WO | 93/22235 A1 | 11/1993 |
| WO | 01/94040 A1 | 12/2001 |
| WO | 02/49458 | 6/2002 |
| WO | 2004/014781 | 2/2004 |

OTHER PUBLICATIONS

Search Report issued in GB 1705724.1 dated Aug. 22, 2017.
International Search Report dated Oct. 13, 2017 in International Application No. PCT/GB2017/051287 filed May 10, 2017.
Examination Report dated Mar. 17, 2022 from the corresponding European Application No. 17724400.1.
Third Party Observations dated Jul. 30, 2021 from the corresponding European Application No. 17724400.1.

* cited by examiner

CONNECTOR

CROSS-REFERENCE TO RELATED APPLICATIONS

This application is a national phase application filed under 35 U.S.C. § 371 of International Application No. PCT/GB2017/051287, filed May 10, 2017, which claims priority to, and the benefit of, Patent Application No. GB 1608280.2, filed May 11, 2016, and Patent Application No. GB 1705724.1, filed Apr. 10, 2017.

The present invention relates to a connector for use in a beverage dispense system and a beverage dispense system incorporating the connector. Furthermore, the present invention relates to methods for monitoring the presence of bubbles in a beverage flow through a beverage dispense system using the sensor.

BACKGROUND

Draught beverages such as lagers and ciders are typically stored within storage kegs inside a cooled cellar/storage room. A beverage line is used to transport the beverage from a storage keg to a dispensing site, such as a dispense font located on a bar. The beverage line is connected to the storage keg using a keg connector.

The beverage line typically passes through a fob detector having a float within a chamber. When beverage is flowing through the beverage line, the beverage buoys up the float. When the storage keg begins to empty, bubbles of carbon dioxide enter the beverage line such that the float sinks to the base of the chamber and seals off the beverage line from the empty storage keg. In order to reopen the beverage line once a new storage keg has been attached, beverage has to be bled from a valve at the top of the fob detector to remove the bubbles from the beverage line.

GB2511851A discloses a bubble detection system which uses an optical sensor located in the keg connector to sense bubbles in the beverage line. When a predetermined level of bubbles is detected in the beverage line (indicating that the beverage supply is approaching depletion), the sensor sends a signal to a valve which closes the beverage line to allow the beverage supply to be changed.

The optical sensor relies on deflection of the light path by bubbles in the beverage between an optical transmitter and an optical receiver. Any build-up of contaminants e.g. yeast within the beverage line will obscure the light path causing the sensor to erroneously indicate the presence of bubbles within the beverage and unnecessarily effect closure of the beverage line.

There is a need for an improved sensor for monitoring beverage flow and effecting closure of the beverage line if bubbles are present within the beverage flow.

There is also a need for a sensor for monitoring beverage identity (e.g. beverage types (such as beer/cider) and beverage brands) within a beverage flow line and for providing information on beverage types to a remote location such as to the beverage outlet head office or to the beverage source supplier (e.g. a brewery). This information can be used for various purposes e.g. to monitor beverage sales and brand performance or to make predictions concerning future supply requirements.

SUMMARY OF THE INVENTION

In a first aspect, the present invention provides a beverage dispense system comprising a beverage flow path for transporting beverage between a beverage supply and a dispensing site, wherein the beverage dispense system comprises an electrical sensor for measuring an electrical parameter of a beverage within the beverage flow path.

Bubbles within a beverage can be an early indication that fobbing is about to commence and thus that the beverage supply is nearly depleted (i.e. the storage keg is nearly empty). The electrical properties of the beverage will change if it contains bubbles (since air/carbon dioxide has a lower dielectric constant than a liquid beverage) and the electrical sensor in the present invention can measure the electrical parameter and/or changes in the electrical parameter to determine if bubbles are present in the beverage.

Unlike the optical sensor, the electrical sensor is unaffected by a build-up of contaminants e.g. yeasts within the beverage flow path.

Furthermore, an electrical sensor can monitor beverage identity (e.g. beverage types (such as beer/cider) and beverage brands) since each beverage type/brand will have unique electrical properties dependent on the nature and level of solutes in the beverage. The electrical sensor can provide feedback to a remote location such as to the beverage outlet head office or to the beverage source supplier (e.g. a brewery). This information can be used for various purposes e.g. to monitor beverage sales and brand performance or to make predictions concerning future supply requirements.

The beverage dispense system is preferably a draught beverage dispense system i.e. a system comprising a dispense font connected to a beverage line (which at least partly defines the beverage flow path) having a distal end for connection to the beverage supply or to a connector connected to the beverage supply. The beverage supply is stored (and thus the distal end of the beverage line is provided) at a location (e.g. a cellar) remote from the dispensing site (e.g. a bar area) where the dispense font is located. A pump may be included to transfer beverage on demand to the dispense font through the beverage line.

In preferred embodiments, the electrical parameter is selected from a group comprising: conductivity, resistivity, dielectric constant, permittivity, capacitance and inductance.

Preferably, the sensor is a capacitive sensor for measuring capacitance/changes in capacitance of the beverage in the beverage flow path. When the beverage in the beverage flow path contains bubbles, the dielectric constant of the beverage in the beverage flow path will decrease and thus the capacitance will decrease.

The sensor may be adapted to measure the absolute value of the electrical parameter to determine the identity of the beverage as each beverage (each type and/or brand) will have its own unique value for each electrical parameter dependent on the nature and level of solutes in the beverage.

The sensor may be adapted for generating an output signal for blocking the beverage flow path when a predetermined value or change in value of the electrical parameter is measured. In this manner, the beverage flow within the beverage flow path can be stopped (and the beverage supply replaced) if the measured electrical parameter/change in electrical parameter indicates that bubbles are present in the beverage flow.

In preferred embodiments, the sensor comprises a downstream electrode and an upstream electrode, each made of electrically conductive material. The upstream electrode is proximal the beverage supply. The downstream electrode is distal the beverage supply. The electrodes are spaced and electrically insulated from one another by an insulating spacer. The insulating spacer may formed of plastics material.

The electrodes may extend into the beverage flow path or they may partly define the beverage flow path.

The insulating spacer may partly define the beverage flow path or may be external to the beverage flow path.

Preferably, the sensor is operable to apply an input voltage and/or current to one of the upstream/downstream electrodes. For example, the sensor may comprise a power source (such a battery) or may be connectable to a power supply.

Preferably, the sensor is adapted to apply an alternating input voltage/current to one of the upstream/downstream electrodes. The sensor may be adapted to apply an alternating input voltage/current having a saw tooth wave form to one of the upstream/downstream electrodes.

The sensor may comprise a piezoelectric crystal. For example, the sensor may be comprise a quartz crystal such as those used in watches. Such quartz crystals have a natural oscillation of around 32 kHz. The sensor may be connectable to a low voltage power supply which feeds a low voltage/DC to the crystal which then provides an alternating voltage/current feed to one of the upstream/downstream electrodes.

The piezoelectric (e.g. quartz) crystal may be mounted on a Printed Circuit Board (PCB) housed outside of the beverage flow path. The PCB may be mounted within the connector or may be mounted externally of the connector e.g. on an outside surface of the connector such as within a housing mounted on the outside surface of the connector.

The sensor is operable to detect a resultant electrical signal (e.g. a resultant output current/voltage) in the other upstream/downstream electrode to that to which the input current/voltage is applied. For example, the sensor may comprise a measuring transducer for detecting the resultant electrical signal. The measuring transducer may be mounted on the PCB.

In preferred embodiments, the sensor is adapted to apply an input current/voltage to the downstream electrode to generate a resultant electrical signal (e.g. for detection by the measuring transducer) in the upstream electrode. Accordingly, the battery/power supply and piezoelectric crystal may be connected to the downstream electrode and the measuring transducer may be connected to the upstream electrode. This arrangement has been found to provide a more responsive sensor as bubbles will be detected earlier as they first pass the upstream electrode in the beverage flow path.

The sensor may further comprise a processor operable to generate the output signal for blocking the beverage flow path when the resultant electrical signal indicates a predetermined value of/change in the electrical parameter. The processor may be mounted on the PCB. In some embodiments the processor may be part of a microcontroller mounted on the PCB.

In some embodiments, the upstream and downstream electrodes are spaced from one another (e.g. by the insulating spacer) by at least 8 mm, preferably by at least 10 mm and optimally by around 55 mm. Increasing the spacing between the upstream and downstream electrodes maximizes the volume of beverage for which the electrical parameter is measured such that the effect of incidental, insignificant bubbles is minimized.

In some embodiments, the upstream electrode comprises an upstream probe or plate and the downstream electrode comprises a downstream probe or plate, each probe/plate extending into the beverage flow path. The upstream and downstream probes/plates may be substantially parallel to one another (i.e. the longitudinal axes of the probes may be parallel or the plates may be substantially parallel to one another).

The probes/plates may extend substantially perpendicularly to the beverage flow path.

One of the upstream/downstream probes/plates may have a longer length than the other with the longer probe/plate being insulated along the portion of its length that is aligned with the shorter probe/plate. This effectively extends the spacing between the electrically conductive portions of the two probes thus minimising the effect of incidental, insignificant bubbles as discussed above.

Probes are preferred as they impede beverage flow within the beverage flow path less than plates.

In other embodiments, the downstream electrode and upstream electrode each comprise a respective tubular electrode each encircling and defining part of the beverage flow path. The upstream tubular electrode may be spaced and electrically insulated from the downstream tubular electrode by a tubular insulating spacer encircling and defining the beverage flow path between the electrodes. In these embodiments, the sensor can monitor the electrical parameter of the beverage without disrupting the beverage flow through the beverage flow path.

The tubular electrodes may be axially aligned or the insulating spacer may comprise a deflection e.g. an L-shaped bend such that the tubular elements are not axially aligned.

The tubular electrodes may be formed of food grade stainless steel.

The sensor may be provided within a connector provided at a distal end of a beverage line, the connector for connecting the beverage line to a beverage supply. In these embodiments, the electrical sensor is for measuring the electrical parameter of the beverage within a connector conduit (which partly defines the beverage flow path). The sensor can then generate an output signal for closing the beverage line when a predetermined value of/change in the electrical parameter is measured.

In preferred embodiments, the connector is as described below for the second aspect.

In a second aspect, the present invention provides a connector for use in a beverage dispense system, the connector defining a conduit for connecting a beverage line to a beverage supply, the connector comprising an electrical sensor for measuring an electrical parameter of a beverage within the connector conduit.

The connector may be directly connectable to the beverage supply e.g. the connector may have a push- or screw-fit connection element. Alternatively, the connector is connectable e.g. by a push- or screw-fit connection element to a standard keg coupler (i.e. a coupler which connects to the top of the keg spear and which has a gas line inlet and a beverage outlet).

Preferably, the beverage line has a distal end (proximal the beverage supply and remote from the point of dispense) and the connector has a second connection element for fixing to the distal end of the beverage line.

By providing the sensor in a connector which connects at the distal end of the beverage line, the sensor can be positioned as close to the beverage supply as possible such that the bubbles preceding fobbing (which is indicative of the impending emptying of the storage keg) can be detected at the earliest possible moment.

In preferred embodiments, the electrical parameter is selected from a group comprising: conductivity, resistivity, dielectric constant, permittivity, capacitance and inductance.

Preferably, the sensor is a capacitive sensor for measuring capacitance and/or changes in capacitance of the beverage in the connector conduit. When the beverage in the connector conduit contains bubbles, the dielectric constant of the beverage in the connector conduit will decrease and thus the capacitance will decrease.

The sensor may be adapted to measure the absolute value of the electrical parameter to determine the identity of the beverage as each beverage (each type and/or brand) will have its own unique value for each electrical parameter dependent on the nature and level of solutes in the beverage.

The sensor may be adapted for generating an output signal for blocking the beverage line when a predetermined value or change in value of the electrical parameter is measured. In this manner, the beverage flow within the beverage line can be stopped (and the beverage supply replaced) if the measured electrical parameter/change in electrical parameter indicates that bubbles are present in the beverage.

In preferred embodiments, the sensor comprises a downstream electrode and an upstream electrode, each made of electrically conductive material. The upstream electrode is proximal the beverage supply. The downstream electrode is distal the beverage supply. The electrodes are spaced and electrically insulated from one another by an insulating spacer. The insulating spacer may formed of plastics material.

The electrodes may extend into the connector conduit or they may partly define the connector conduit.

The insulating spacer may partly define the connector conduit or may be external to the connector conduit. Where it is external to the connector conduit, it may comprise bores through which the electrodes extend.

Preferably, the sensor is adapted to apply an input voltage and/or current to one of the upstream/downstream electrodes. For example, the sensor may comprise a power source (such a battery) or may be connectable to a power supply.

Preferably, the sensor is adapted to apply an alternating input voltage/current to one of the upstream/downstream electrodes. The sensor may be adapted to apply an alternating input voltage/current having a saw tooth wave form to one of the upstream/downstream electrodes.

The sensor may comprise a piezoelectric crystal. For example, the sensor may comprise a quartz crystal such as those used in watches. Such quartz crystals have a natural oscillation of around 32 kHz. The sensor may be connectable to a low voltage power supply which feeds a low voltage/DC to the crystal which then provides an alternating voltage/current feed to one of the upstream/downstream electrodes.

The piezoelectric (e.g. quartz) crystal may be mounted on a Printed Circuit Board (PCB) housed outside of the beverage flow path. The PCB may be mounted within the connector or may be mounted externally of the connector e.g. on an outside surface of the connector such as within a housing mounted on the outside surface of the connector.

The sensor is operable to detect a resultant electrical signal (e.g. a resultant output current/voltage) in the other upstream/downstream electrode to that to which the input current/voltage is applied. For example, the sensor may comprise a measuring transducer for detecting the resultant electrical signal. The measuring transducer may be mounted on the PCB.

In preferred embodiments, the sensor is adapted to apply an input current/voltage to the downstream electrode to generate a resultant electrical signal (e.g. for detection by the measuring transducer) in the upstream electrode. Accordingly, the battery/power supply and piezoelectric crystal may be connected to the downstream electrode and the measuring transducer may be connected to the upstream electrode. This arrangement has been found to provide a more responsive sensor as bubbles will be detected earlier as they first pass the upstream electrode in the beverage flow path.

The sensor may further comprise a processor operable to generate an output signal for blocking the beverage line when the resultant electrical signal indicates a predetermined value of/change in the electrical parameter. The processor may be mounted on the PCB.

The processor may be part of a microcontroller or system on a chip (SoC) which is mounted on the PCB. In addition to the processor, the microcontroller may further comprise an interface to allow a user to update software, run diagnostic software and/or receive data from the microcontroller. For example, the microcontroller may collect data relating to the amount of beverage dispensed, the time elapsed since the line was cleaned, the identity of the beverage dispensed, the beverage temperature in the connector, gas bottle fill level indication, and/or gas leak detection. This data can be provided to the user or to a remote location such as to the beverage outlet head office or to the beverage source supplier. For example the data may be provided to an app running on a smartphone or other mobile device, or application software running on a computer. Additionally or alternatively, to enable a user to receive data from the microcontroller, the PCB may have at least one port such as a USB port. Preferably, the microcontroller may be accessed wirelessly, for example via Bluetooth using an appropriate Bluetooth module mounted on the PCB.

The microcontroller may also be configured to generate an output signal to operate one or more indicators. In some embodiments the one or more indicators may be used for providing an indication that the sensor has generated a signal to block the beverage line, and/or for providing an indication that a cleaning mode is effected. Preferably an indicator may be an LED. In some embodiments the one or more LEDs may be mounted on the PCB such that they are visible to a user, for example the PCB may be mounted externally of the connector and the LEDs may be viewable through a window in a housing containing the PCB.

In some embodiments, the upstream and downstream electrodes are spaced from one another (e.g. by the insulating spacer) by at least 8 mm, preferably by at least 10 mm and optimally by around 55 mm. Increasing the spacing between the upstream and downstream electrodes maximizes the volume of beverage for which the electrical parameter is measured such that the effect of incidental, insignificant bubbles is minimized.

In some embodiments, the upstream electrode comprises an upstream probe or plate and the downstream electrode comprises a downstream probe or plate, each probe/plate extending into the beverage flow path. The upstream and downstream probes/plates may be substantially parallel to one another (i.e. the longitudinal axes of the probes may be parallel or the plates may be substantially parallel to one another).

The probes/plates may extend substantially perpendicularly to the longitudinal axis of the connector conduit.

The probes/plates may be of any suitable length, preferably ranging between 10 mm & 20 mm. One of the upstream/downstream probes/plates may have a longer length than the other with the longer probe/plate being insulated along the portion of its length that is aligned with the shorter probe/plate. This effectively extends the spacing between the electrically conductive portions of the two probes thus minimising the effect of incidental, insignificant bubbles as discussed above.

Probes are preferred as they impede beverage flow within the beverage flow path less than plates. In some embodiments the probes are less than 5 mm in diameter, preferably less than 3 mm in diameter, and optimally around 1 mm in diameter.

In other embodiments, the downstream electrode and upstream electrode each comprise a respective tubular electrode each encircling and defining part of the connector conduit. The upstream tubular electrode may be spaced and electrically insulated from the downstream tubular electrode by a tubular insulating spacer encircling and defining the connector conduit between the electrodes. In these embodiments, the sensor can monitor the electrical parameter of the beverage without disrupting the beverage flow through the connector conduit.

The tubular electrodes may be axially aligned or the insulating spacer may comprise a deflection e.g. an L-shaped bend such that the tubular elements are not axially aligned.

The tubular electrodes may be formed of food grade stainless steel.

The connector may have, for example, a substantially L-shaped body or a substantially tubular body. In some embodiments, the connector body may define the connector conduit.

Where the connector comprises a substantially tubular body, the connector conduit may be substantially linear. In these embodiments, the downstream electrode and upstream electrode may each comprise a respective tubular electrode each encircling and defining part of the connector conduit, the tubular electrodes being axially aligned. The tubular insulating spacer extends between the upstream and downstream tubular electrodes (being axially aligned therewith) and defines the connector conduit therebetween.

In alternative embodiments, the downstream electrode may comprise a downstream probe extending perpendicularly across (either partly or completely across) the connector conduit and the upstream electrode may comprise an upstream probe extending perpendicularly across (either partly or completely across) the connector conduit.

Where the connector comprises an L-shaped body, the connector conduit will be L-shaped such that the conduit has an upstream branch and a downstream branch which meet at around 90° at a bend/elbow. The connector conduit may be defined by the L-shaped connector body. The radius of curvature of the bend/elbow of the L-shape connector conduit is preferably selected so as to reduce the risk of an air pocket forming from gas trapped within the bend/elbow. The upstream branch of the connector is proximal the beverage supply. The downstream branch of the connector is distal the beverage supply.

In these embodiments, the downstream and upstream probes may be provided at or around the bend/elbow of the L-shaped connector conduit.

In these embodiments, one of the upstream or downstream probes extends substantially axially within a first branch of the L-shaped connector conduit it, and the other one of the upstream or downstream probes extends perpendicularly across a second branch of the L-shaped In some embodiments, the downstream probe may extend substantially perpendicularly to the beverage flow path within the connector. The upstream probe may extend substantially parallel to the beverage flow path within the connector.

For example, the upstream probe may extend substantially axially within one branch of the L-shaped connector conduit whilst the downstream probe may be substantially parallel to the upstream probe extending perpendicularly across the other branch of the L-shaped connector conduit. In these embodiments, the upstream probe may be longer than the downstream probe and insulated along part of its length as discussed above.

In other embodiments, the downstream probe may extend substantially parallel to the beverage flow within the connector. The upstream probe may extend substantially perpendicular to the beverage flow path within the connector.

For example, the downstream probe may extend substantially axially within one branch of the L-shaped connector conduit whilst the upstream probe may be substantially parallel to the downstream probe extending perpendicularly across the other branch of the L-shaped connector body. In these embodiments, the downstream probe may be longer than the upstream probe and insulated along part of its length as discussed above. In such embodiments, the upstream probe is able to detect the presence of bubbles which take the shortest route along the internal bend of the L-shaped connector body which ensures swift detection.

In some embodiments, the upstream and downstream probes have different diameters which correspond to complementary apertures in the connector body. In this way, it can be ensured that the correct probe is inserted in the correct aperture during manufacture of the connector.

Preferably, the connector contains a connector cooling circuit for cooling the beverage within the connector. In this way any beverage can be maintained at temperature at which microorganism growth is limited.

The connector cooling circuit may comprising a connector cooling line and a connector cooling return line for carrying chilled cooling medium, the cooling lines being in heat exchange relationship with the connector conduit.

Alternatively, the connector may comprise a cooling channel for carrying chilled cooling medium, the cooling channel surrounding the connector conduit i.e. the connector conduit and cooling channel may be concentric. The cooling channel may be integrally formed with the connector body.

The insulating spacer may be integrally formed with the connector body.

Where the connector comprises a cooling channel, the insulating spacer may extend through or define the end wall of the cooling channel. The electrodes may pass through bores in the insulating spacer into the connector conduit. In this way, the electrodes are electrically isolated from the cooling medium in the cooling channel. The electrodes may be mounted on a mounting plate which abuts the outer surface of the connector body/insulating spacer. The electrodes may each comprise a respective compression washer at their point of attachment to the mounting plate to prevent leakage of beverage from the connector conduit.

Where the connector comprises a cooling channel, it is preferable that the PCB is mounted on an outside surface of the connector body e.g. within a housing mounted on the outside surface of the connector body.

The housing may be provided on the outside surface of the connector body in abutment with the mounting plate (on the opposing side from the electrodes).

The fixing of the housing against the mounting plate may compress the compression washers thus sealing the electrodes within the insulating spacer and preventing leakage of beverage from the connector conduit.

For example, the PCB housing may comprise a channel in its base for receiving the mounting plate. It may be a T-shaped channel i.e. having a vertical channel portion and a horizontal channel portion. It may have at least one open end perpendicular to the longitudinal axis of the channel such that the mounting plate can slide into the horizontal portion of the channel from the open end. The mounting plate may be retained within the horizontal portion of the channel by abutment against flanges extending at least partly along the length of the channel which define the vertical portion of the channel.

The exterior surface of the connector may comprise a mounting platform against which the mounting plate abuts. The mounting platform may be received in the channel, e.g. in the horizontal portion of the channel, along with the mounting plate such that the compression washers are compressed against the mounting platform.

The mounting platform may be tapered such that the compression of the compression washers is maximized. The mounting platform may be integral with the connector body and/or the insulating portion.

In a third aspect, the present invention provides a bubble detection system for use in a beverage dispense system, the bubble detection system comprising a connector according to the second aspect and a valve operable to close the beverage line upon receipt of the output signal from the electrical sensor.

The bubble detection system preferably comprises an electronic control unit for receiving the output signal from the electrical sensor (e.g. from the processor in the sensor) and, in response to the output signal from the electrical sensor, sending a signal to the valve to close the beverage line. The signal between the electrical sensor and the electronic control unit may be transmitted via a wire. The electronic control unit may comprise a microcontroller, such as the microcontroller discussed above.

In a fourth aspect, the present invention provides a beverage dispense system comprising a beverage line connectable to a beverage supply for transporting beverage from the beverage supply to a dispensing site and a connector according to the second aspect, wherein the connector is connected to a distal end of the beverage line.

In a fifth aspect, the present invention provides a beverage dispense system comprising a beverage line connectable to a beverage supply for transporting beverage from the beverage supply to a dispensing site and a bubble detection system according to the third aspect, wherein the connector of the bubble detection system is connected to a distal end of the beverage line.

In the fourth and fifth aspects, the beverage dispense system is preferably a draught beverage dispense system as described above for the first aspect.

In a sixth aspect, the present invention provides a method of detecting bubbles within a beverage flow path extending between a beverage supply and a dispensing site in a beverage dispense system, the method comprising measuring an electrical parameter of a beverage within the beverage flow path using an electrical sensor.

The beverage dispense system is preferably a draught beverage dispense system as described above for the first aspect.

In preferred embodiments, the method comprises measuring an electrical parameter selected from a group comprising: conductivity, resistivity, dielectric constant, permittivity, capacitance and inductance.

Preferably, the sensor is a capacitive sensor and the method comprises measuring capacitance/changes in capacitance of the beverage in the beverage flow path. When the beverage in the beverage flow path contains bubbles, the dielectric constant of the beverage in the beverage flow path will decrease and thus the capacitance will decrease.

The method may comprise measuring the absolute value of the electrical parameter to determine the identity of the beverage as each beverage (each type and/or brand) will have its own unique value for each electrical parameter dependent on the nature and level of solutes in the beverage.

The method may comprise generating an output signal for blocking the beverage flow path when a predetermined value or change in value of the electrical parameter is measured. In this manner, the beverage flow within the beverage flow path can be stopped (and the beverage supply replaced) if the measured electrical parameter/change in electrical parameter indicates that bubbles are present in the beverage flow.

In preferred embodiments, the sensor is as described above for the beverage system of the first aspect.

The method may comprise applying a current/voltage (e.g. an alternating input voltage/current) to one of the upstream/downstream electrodes of the sensor. The method may comprise applying an alternating input voltage/current having a saw tooth wave form to one of the upstream/downstream electrodes.

The method may comprise detecting a resultant electrical signal (e.g. a resultant output current/voltage) in the other upstream/downstream electrode to that to which the input current/voltage is applied e.g. using a measuring transducer.

In preferred embodiments, the method comprises applying an input current/voltage to the downstream electrode to generate a resultant electrical signal in the upstream electrode (and measuring the resultant electrical signal at the upstream electrode (e.g. using the measuring transducer)).

The sensor may be provided within a connector as described in the second aspect. In these embodiments, the method comprises measuring the electrical parameter of the beverage within the connector conduit (which partly defines the beverage flow path).

In some embodiments, the method further comprises cooling the beverage within the connector conduit/beverage flow path within the connector using a connector cooling circuit or a cooling channel as described above for the second aspect.

BRIEF DESCRIPTION OF DRAWINGS

Preferred embodiments of the present invention will now be described with reference to the accompanying Figures in which.

DETAILED DESCRIPTION OF THE INVENTION

Figure 1:
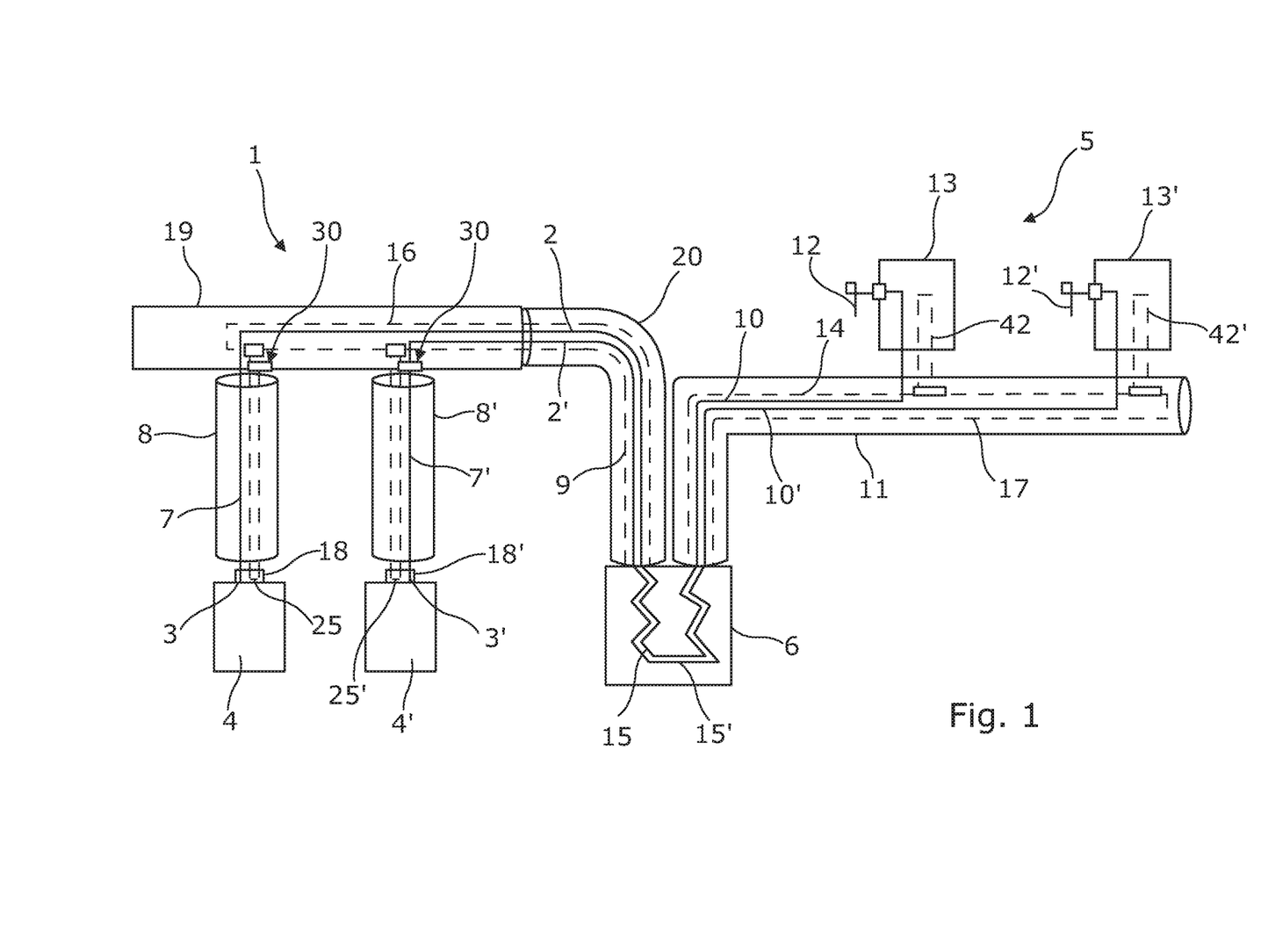
FIG. 1 shows a schematic representation of a first embodiment of the beverage dispense system according to the present invention.

FIG. 1 shows a draught beverage dispense system 1 for dispensing two beverages. The system comprises two beverage lines 2, 2' each having a distal end 3, 3' connectable to a respective beverage supply 4, 4' for transporting beverage from each beverage supply 4, 4' to a dispensing site 5 having two dispense fonts 13, 13' each with a respective tap 12, 12' through which the beverage is dispensed.

The system further comprises a cooler 6 for cooling beverage. The cooler 6 is adapted to generate cooling medium. The cooler 6 comprises an ice bank and a cooling medium reservoir (not shown), the cooling medium in the cooling medium reservoir being cooled by the ice bank.

Each beverage line 2, 2' comprises a first beverage line portion 7, 7' extending from the respective distal end 3, 3' to the cooler 6. Each first beverage line portion 7, 7' extends within a first insulated carrier which is made up of a respective distal first insulated carrier portion 8, 8' which is a python-type insulated carrier, a foam core 33 of a manifold 19 and a combined proximal first insulated carrier portion which is a further python type insulated carrier 20. A solenoid valve 30, 30' is provided in the beverage line 2, 2' within the manifold 19. The solenoid valve 30, 30' is a two-way valve which can either direct beverage from the beverage supply 4, 4' towards the dispensing site 5, 5' or towards a bleed line (not shown) which is directed towards a drain or storage tank.

A first cooling line 9 for transporting cooling medium (generated by the cooler 6) through the proximal first insulated carrier portion (a python-type insulated carrier 20), the core 33 of the manifold 19 and then through the two distal first insulated carrier portions 8, 8' is provided so as to allow heat exchange between the cooling medium in the first cooling line 9 and the beverage in the first beverage line portions 7, 7'.

The first cooling line 9 forms part of a first cooling circuit, the first cooling circuit including the first cooling line 9 extending from the cooler 6 through the proximal first insulated carrier portion 20, the manifold 19 and distal first insulated carrier portions 8, 8' to each beverage supply 4, 4' and a first return line 16 returning the cooling medium to the cooling medium reservoir of the cooler 6. The first cooling line 9 and first return line 16 typically have a diameter of 9.5 mm (in the distal first insulated carrier portions) and 15 mm (within the manifold 19 and the proximal first insulated carrier portion).

The beverage lines 2, 2' further comprise a respective second beverage line portion 10, 10' for transporting beverage from the cooler 6 to the respective tap 12, 12' on the respective dispense font 13, 13' at the dispensing site 5 through a second insulated carrier 11. The second insulated carrier 11 comprises a second cooling line 14 for transporting cooling medium (from the cooler 6) through the second insulated carrier 11 so as to allow heat exchange between the cooling medium in the second cooling line 14 and the beverage in the second beverage line portions 10, 10'.

The second cooling line 14 preferably forms part of a second cooling circuit, the second cooling circuit including the second cooling line 14 extending from the cooler 6 through the second insulated carrier 11 to the dispensing site 5 and a second return line 17 extending from the dispensing site 5 through the second insulated carrier 11 to the cooling medium reservoir of the cooler 6. The second cooling line and second return line typically have a diameter of 15 mm.

The second cooling circuit also includes a font cooling circuits 42, 42' which carry cooling medium into the font to allow heat exchange with the second beverage line portion 10 in the font to maintain the low temperature of the beverage and, optionally, to promote formation of condensation on the outer surface of the font (for aesthetic reasons). The lines in the font cooling circuit typically have a diameter of around 9.5 mm (⅜ inch).

Each beverage line 2, 2' includes a respective cooling beverage line portion 15, 15' that passes through the cooling medium reservoir in the cooler 6 from the first beverage line portion 7, 7' to the respective second beverage line portion 10, 10'. Each cooling beverage line portion 15, 15' is a coiled portion that can be immersed in the cooling medium in the reservoir. The amount of coil immersed can be varied to determine the extent of heat exchange and hence the extent of cooling of the beverage.

Figure 2:
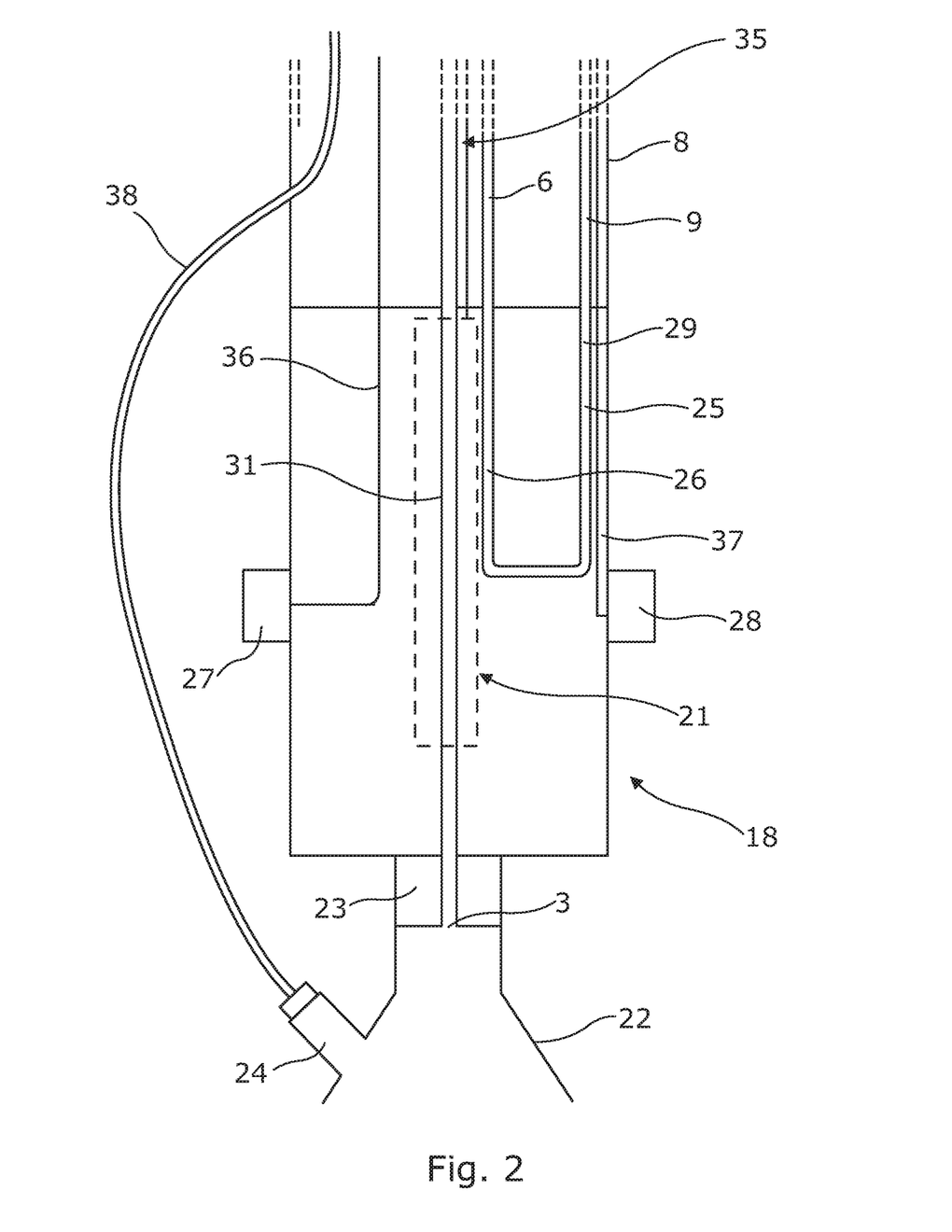
FIG. 2 shows a schematic view of a connector according to a first embodiment of the present invention.

At the distal ends 3, 3' of the beverage lines 2, 2' is provided a respective connector 18, 18' as shown in FIG. 2.

The connector 18 has a tubular body 36 and a push fit element 23 for fitting to a standard keg coupler 22 (i.e. a coupler which connects to the top of the keg spear) provided on the beverage supply 4.

The connector 18 defines a connector conduit 31 extending between the beverage line 2 and the beverage supply 4. The connector conduit 31 and the associated beverage line 2 define a beverage flow path for transporting beverage between the beverage supply 4 and the dispense font 13.

The standard keg coupler 22 comprises a gas inlet 24 connected to a gas line 28 which is connected to a gas supply for supplying gas to the beverage supply 4 to force the beverage from beverage supply 4 along the beverage flow path i.e. through the connector conduit 31 and along the beverage line 2.

The connector 18 comprises an electrical capacitance sensor 21 for measuring the capacitance and/or changes in the capacitance of a beverage within the connector conduit 31.

The connector 18 contains a connector cooling circuit 25 comprising a connector cooling line 29 for receiving cooling medium from the first cooling line 9 and a connector cooling return line 26 for returning cooling medium to the first cooling return line. The connector cooling medium circuit is in heat exchange relationship with the connector conduit for cooling the beverage as it leaves the storage keg.

The connector 18 and solenoid valve 30 form a bubble detection system according to the third aspect of the present invention.

The sensor 21 is adapted to generate an output signal for closing the valve 30 to block the beverage line 2 when a predetermined value or change in value of the conductance is measured. The output signal is transferred from the sensor 21 to the valve 30 through a wire 35.

In this manner, the beverage flow within the beverage line 2 can be stopped (and the beverage supply replaced) if the measured electrical parameter/change in electrical parameter indicates that bubbles are present in the beverage.

The connector 18 further comprises an indicator 27 for providing an indication when the sensor 21 has generated a signal for the valve 30 to close the beverage line 2. The indicator 27 is a light which changes from green to red when the beverage line 2 is closed. The red light shines onto the beverage supply (storage keg) to highlight to the user which keg needs changing.

The connector further comprises a re-set actuator 28 (button) which is operable to generate a signal to re-open the valve 30 and thus the beverage line 2 once the beverage supply 4 has been replenished (i.e. the storage keg changed). The re-set actuator 28 is also operable to re-set the indicator 27 i.e. to turn the red light back to green. Preferably the re-set actuator is prominently positioned on the connector 18 for ease of identification and use.

The re-set actuator may be operated in a first mode of actuation by a single, short depression of the button and, in the first mode of actuation, the beverage line 2 is opened at the valve 30 to a bleed line directed towards a drain or storage tank.

Additionally, the re-set actuator may be operated in a second mode of actuation by a single, prolonged depression of the button. The second mode of actuation of the re-set actuation is only effected when a water or cleaning fluid supply is attached to the distal end 3 of the beverage line 2. The second mode of actuation of the re-set actuator causes the opening of the valve 30 and thus the beverage line 2 and for the water/cleaning fluid to be pumped through the beverage line 2 to effect cleaning. This need only be effected once every 4 weeks.

Alternatively, the connector may comprise a second actuator which may be operated to trigger a cleaning mode. The cleaning mode may be effected when a water or cleaning fluid supply is attached to the distal end 3 of the beverage line 2. The second actuator may be discreet and recessed into the connector 18 to avoid accidental operation of the second actuator. The second actuator may also need to be depressed for longer than the re-set actuator in order to be actuated to avoid accidental operation.

The connector 18 further comprises a second indicator for providing an indication of a cleaning mode being effected, by either a second mode of actuation of the re-set actuator or by operation of the second actuator. The second indicator is a light which is switched on when the cleaning mode is effected.

Figure 3:
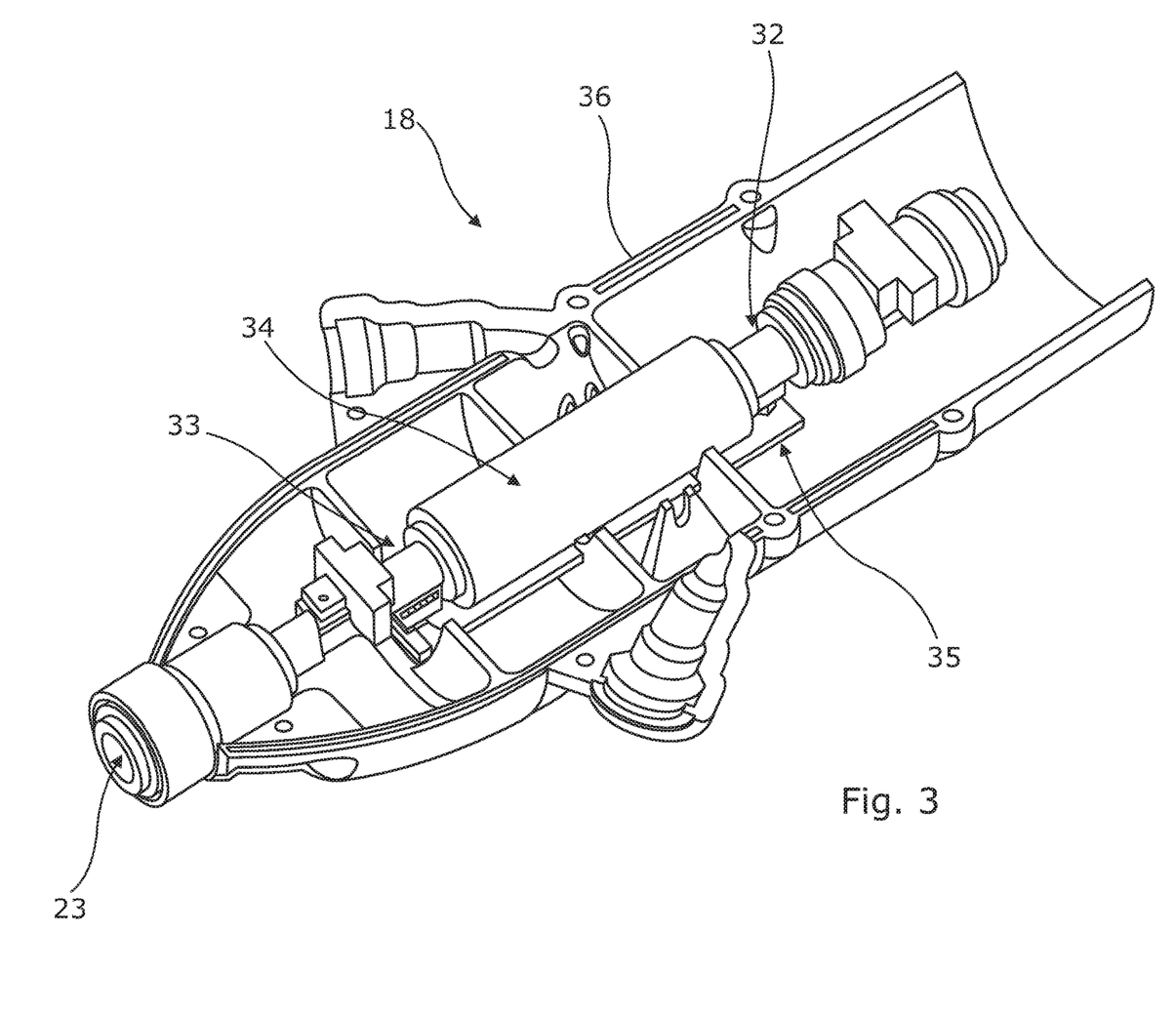
FIG. 3 shows details of a sensor for use in the connector shown in FIG. 2.

FIG. 3 shows further features of one embodiment of the connector 18 shown in FIG. 2. In particular, FIG. 3 shows details of a capacitive sensor 21 for measuring the capacitance of a beverage within the connector conduit.

The sensor comprises a downstream tubular electrode 32 (distal the beverage supply 4) and an upstream tubular electrode 33 (proximal the beverage supply 4).

The tubular electrodes 32, 33 are axially aligned and each encircles and defines part of the connector conduit 31. The upstream tubular electrode 32 is spaced from and is electrically insulated from the downstream tubular electrode 32 by a tubular insulating spacer 34 (made of plastic material). The tubular insulating spacer encircles and defines the connector conduit between the tubular electrodes 32, 33. The tubular electrodes 32, 33 are made of food grade stainless steel.

The spacing between the upstream and downstream electrodes 32, 33 is around 55 mm.

The sensor 21 further comprises a Printed Circuit Board (PCB) 35 which is located within the connector 18. Mounted on the PCB 35 is a quartz crystal (such as that used in a wristwatch). The quartz crystal is provided with a permanent low voltage/current feed and is are operable to apply an alternating voltage/current having a saw tooth wave form and a frequency of 32 kHz to the downstream tubular electrode 32.

Also mounted on the PCB 35 is a measuring transducer (not shown) for detecting a resultant alternating voltage/current signal in the upstream tubular electrode 33 and a processor (not shown) operable to generate the output signal (along wire 35) for closing the valve 30 to block the beverage line 2 when the resultant alternating voltage/current indicates a predetermined value of/change in capacitance.

When the beverage in the connector conduit 31 contains bubbles, the dielectric constant of the beverage in the connector conduit 31 is smaller and thus the capacitance is smaller than when a beverage containing no bubbles is present in the connector conduit. Accordingly, when the measuring transducer detects a resultant signal that indicates a drop in capacitance below a certain level, it can be deduced that bubbles are present in the beverage and thus the sensor 21 can effect closure of the valve 30 to close the beverage line 2. Preferably the sensor 21 is able to close the valve 30 before any detected gas reaches the valve 30 in order to keep bubbles out of the beverage line 2. This may be achieved by a short reaction time of the sensor 21 and short valve activation time, and may also be dependent on the proximity of the valve 30 to the sensor 21.

For example, when applying a saw tooth alternating voltage of 6 v and a frequency of 32 kHz to the downstream tubular electrode 31, a resultant alternating voltage signal would have an amplitude of between approximately 2-4.5 V if bubbles were present in the beverage—a beverage having no fobbing (i.e. no significant number of bubbles) would give a resultant alternating voltage signal with an amplitude greater than 4.5 V.

The absolute value of the capacitance can be used to determine the identity of the beverage in the connector conduit 31 as each beverage has its own unique value of capacitance depending on the level/nature of solutes present. For example, when applying a saw tooth alternating voltage with a voltage of 6 v and a frequency of 32 kHz to the downstream tubular electrode 31 the resultant voltages shown in Table 1 were produced in the upstream tubular electrode 32.

TABLE 1

| Fluid Identity | Voltage (v) |
| --- | --- |
| Cleaning fluid | 6.0 |
| Fosters ™ | 5.5 |
| John Smith's Extra Smooth ™ | 5.4 |
| Strongbow ™ | 4.6 |
| Water | 3.7 |
| Air | 2.0 |

Information on the beverage identity can be provided to a remote location such as to the beverage outlet head office or to the beverage source supplier (e.g. a brewery). This information can be used for various purposes e.g. to monitor beverage sales and brand performance or to make predictions concerning future supply requirements.

To this end, a microcontroller may be mounted on the PCB which comprises the measuring transducer and processor. The microcontroller may collect data relating to the amount of beverage dispensed, the time elapsed since the line was cleaned, the identity of the beverage dispensed, the beverage temperature in the connector, gas bottle fill level indication, and/or gas leak detection, and this data can be provided to the user or to a remote location. For example the data may be provided to an app running on a smartphone or other mobile device, or application software running on a computer.

Additionally or alternatively, to enable a user to receive data from the microcontroller, the PCB may have at least one port such as a USB port. Preferably, the microcontroller may be accessed wirelessly, for example via Bluetooth using an appropriate Bluetooth module mounted on the PCB. A port or wireless connection may also be used to update software or run diagnostic software.

Figure 4:
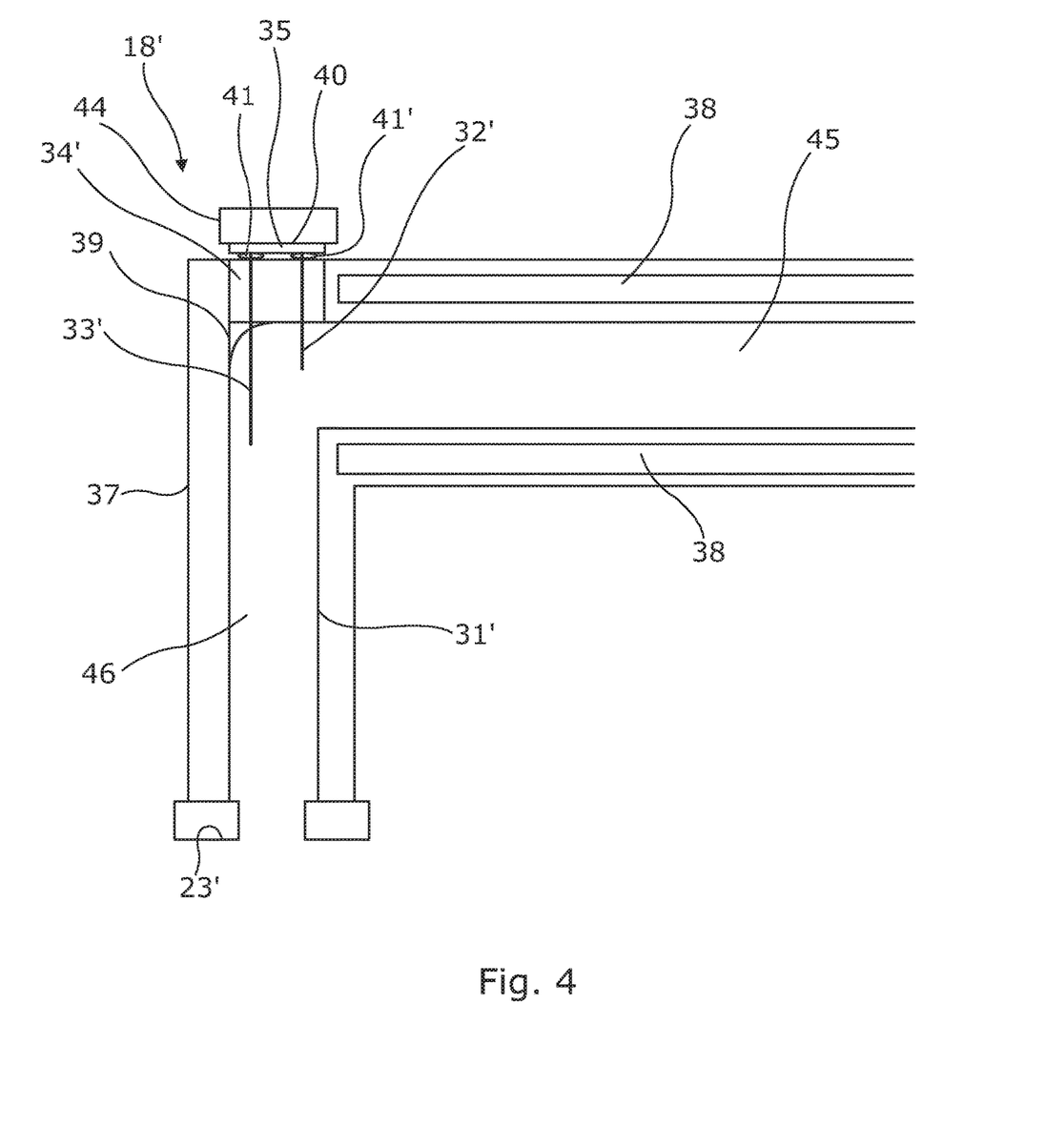
FIG. 4 shows a schematic view of a connector according to a second embodiment of the present invention.

FIG. 4 shows another embodiment of a connector 18 according to the present invention.

The connector 18' has a push fit element 23' for connection to a beverage supply 4 via a standard keg coupler 22' (not shown in FIG. 4). The standard keg coupler 22' is as described above.

The connector 18' comprises an L-shaped body 37 which defines an L-shaped connector conduit 31'. The L-shaped body is formed of an acrylic polymer such as Diakon® PMMA. The conduit 31' is curved at the bend/elbow 39 so as to reduce the risk of an air pocket forming from gas trapped within the bend/elbow.

The connector 18' also comprises a cooling channel 38 for carrying chilled cooling medium. The cooling channel 38 is integrally formed in the connector body 37 and surrounds part of the L-shaped connector conduit 31' i.e. the cooling channel 28 and the connector conduit 31' are concentric.

The connector 18' further comprises a sensor 21' comprising an upstream electrode probe 33' and a downstream electrode probe 32' made of food grade stainless steel, having a 1 mm diameter and spaced apart from each other by 8 mm.

The electrode probes 32', 33' pass through bores in an insulating spacer 34' which is integral with the connector body 37 and which defines the end of the cooling channel 38. The electrode probes 33, 32' extend to the exterior of the connector body 37 through the bores in the insulating portion 34'. In this way the electrodes are electrically isolated from the cooling medium in the cooling channel 38. The probes 32', 33' may have different diameters, corresponding to different bore diameters. This ensures that the probes 32', 33' are inserted in the correct orientation during manufacture of the connector 18'.

The electrodes are mounted on a mounting plate 40 which abuts the outer surface of the insulating spacer 34'. The electrodes also comprise a respective compression washers 41, 41' (e.g. having a diameter of 3 mm with an ID of around 0.8 mm) at their point of attachment to the mounting plate to prevent leakage of beverage from the connector conduit 37. Although not shown in FIG. 4, the connector 18' may comprise a mounting platform interposed between the insulating portion 34' and the mounting plate 40.

The electrode probes 32', 33' are substantially parallel to one another and extend into the beverage flow path within the connector conduit 31'.

The electrode probes 32, 33' are provided at the elbow/bend of the L-shaped connector conduit 31'. The downstream probe 32' extends substantially perpendicular to the beverage flow path and the upstream probe 33' extends substantially parallel to the beverage flow path within the connector conduit.

That is, the downstream probe 32' extends perpendicularly across the downstream branch 45 of the L-shaped connector conduit and the upstream probe 33' extends substantially axially within the upstream branch 46 of the L-shaped connector conduit such that the two probes are parallel.

The upstream probe 33' has a longer length than the downstream probe 32' and is insulated along a portion of its length which is aligned with the shorter downstream probe 32'. The spacing between the conductive portions of the probes which are exposed to beverage in the L-shaped connector conduit 37 is therefore effectively extended.

The sensor 21' also comprises a PCB 35' which is mounted on an outside surface of the connector body within a housing 44 which is mounted onto the outside surface of the connector body 37 in abutment with the mounting plate 40. The housing 44 comprises a T-shaped channel (not shown) having a vertical channel portion and a horizontal channel portion. The mounting plate 44 and tapered mounting platform (not shown) are retained and forced towards one another within the horizontal portion of the channel.

The fixing of the housing 44 against the mounting plate 40/mounting platform compresses the compression washers 41, 41' thus sealing the electrode probes 32', 33' within the insulating spacer 34' and preventing leakage of beverage from the L-shaped connector conduit 37.

Mounted on the PCB 35 is a quartz crystal (such as that used in a wristwatch). The quartz crystal is provided with a permanent live voltage feed and is operable to apply an alternating voltage/current having a saw tooth wave form and a frequency of 32 kHz to the downstream electrode probe 32'.

Also mounted on the PCB 35 is a measuring transducer (not shown) for detecting a resultant alternating voltage/current signal in the upstream electrode probe 33'.

The connector 18' shown in FIG. 4 can replace the connector 18 shown in FIGS. 2 and 3 in the draught beverage dispense system 1 shown in FIG. 1.

The sensor 21' is adapted to generate an output signal for closing the valve 30 to block the beverage line 2 when a predetermined value or change in value of the conductance is measured. Preferably the sensor 21' is able to close the valve 30 before any detected gas reaches the valve 30 in order to keep bubbles out of the beverage line 2. This may be achieved by a short reaction time of the sensor 21' and short activation time of the valve 30, and may also be dependent on the proximity of the valve 30 to the sensor 21'.

In this manner, the beverage flow within the beverage line 2 can be stopped (and the beverage supply replaced) if the measured electrical parameter/change in electrical parameter indicates that bubbles are present in the beverage.

When the beverage in the connector conduit 31' contains bubbles, the dielectric constant of the beverage in the connector conduit 31' is smaller and thus the capacitance is smaller than when a beverage containing no bubbles is present in the connector conduit 31'. Accordingly, when the measuring transducer detects a resultant signal that indicates a drop in capacitance below a certain level, it can be deduced that bubbles are present in the beverage and thus the sensor 21' can effect closure of the valve 30 to close the beverage line 2.

Figure 5:
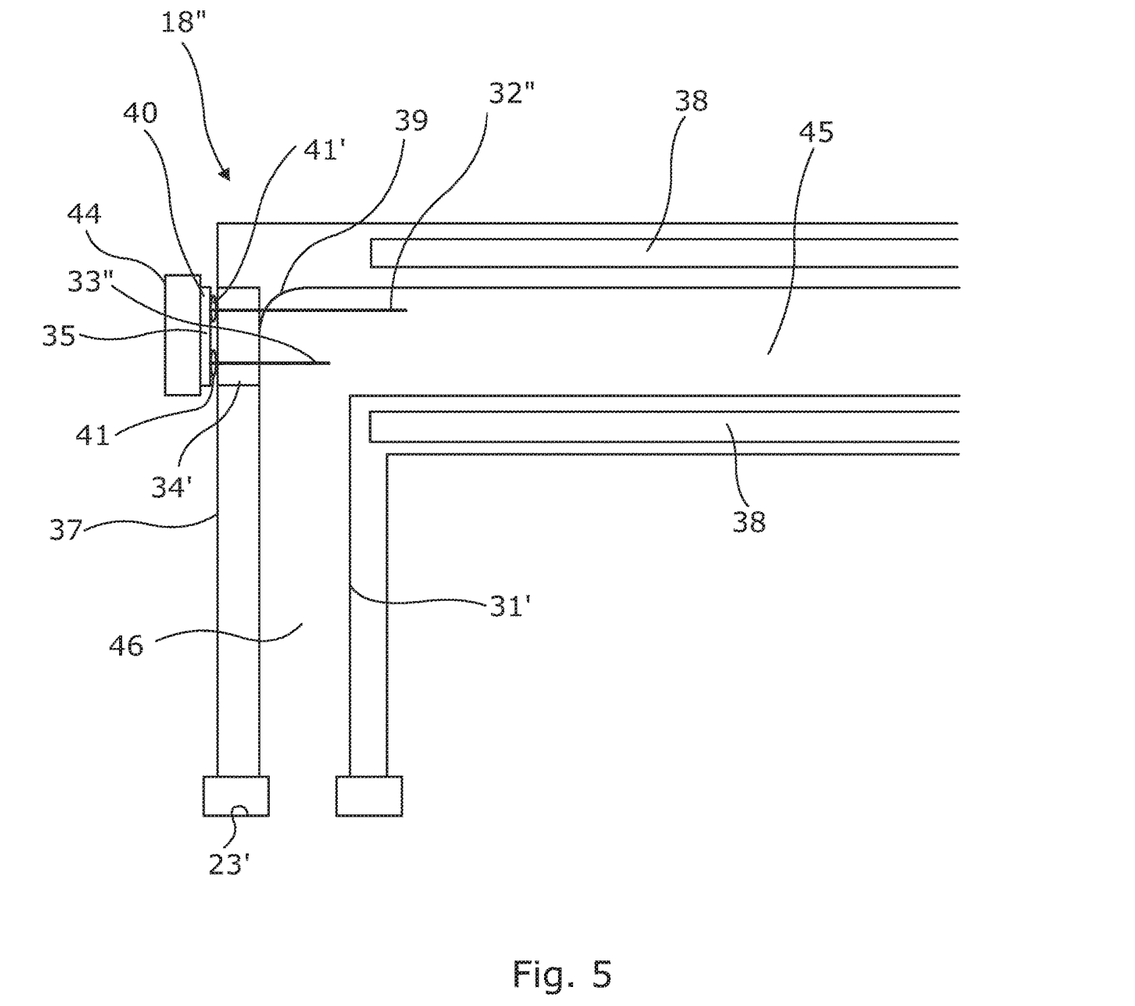
FIG. 5 shows a schematic view of a connector according to a third embodiment of the present invention.

FIG. 5 shows another embodiment of a connector 18" according to the present invention. The connector 18" shown in FIG. 5 can replace the connector 18 shown in FIGS. 2 and 3 in the draught beverage dispense system shown in FIG. 1.

The connector 18" comprises an L-shaped body 37 to define an L-shaped connector conduit 31", similar to the embodiment shown in FIG. 4. Parts having same reference numerals are alike, and no further discussion of those parts is required.

The electrode probes 32", 33" are provided at the elbow/bed of the L-shaped connector conduit 31". The downstream probe 32" extends substantially parallel to the beverage flow path and the upstream probe 33" extends substantially perpendicular to the beverage flow path within the connector conduit. That is, the downstream probe 32" extends substantially axially within the downstream branch 45 of the L-shaped connector conduit and the upstream probe 33" extends perpendicularly across the upstream branch 46 of the L-shaped connector conduit such that the two probes are parallel.

The downstream probe 32" has a longer length than the upstream probe 33" and is insulated along a portion of its length which is aligned with the shorter upstream probe 33". The spacing between the conductive portions of the probes which are exposed to beverage in the L-shaped connector conduit 31" is therefore effectively extended.

The sensor 21' is adapted to apply an input current/voltage to the downstream probe 32" to generate a resultant electrical signal (e.g. for detection by the measuring transducer) in the upstream probe 33". Accordingly, the battery/power supply and piezoelectric crystal may be connected to the downstream probe 32" and the measuring transducer may be connected to the upstream probe 33". This arrangement provides a more responsive sensor as bubbles will be detected earlier as they first pass the upstream probe 33" in the beverage flow path. In addition, due to the placement of the upstream probe 33", it is able to detect the presence of bubbles which that the shortest route along the internal bend of the L-shaped connector conduit 31" which ensures swift detection of bubbles.

The connectors 18', 18" shown FIGS. 4 and 5 also comprise a re-set and second actuators, and may further indicators as discussed above with respect to FIGS. 2 and 3. These have been omitted from the figures for clarity.

The invention claimed is:

1. A connector for use in a beverage dispense system, the connector defining a conduit for connecting a beverage line to a beverage supply, the connector comprising an electrical sensor configured to measure changes in an electrical parameter of a beverage within the connector conduit, the sensor comprises a processor operable to generate an output signal for blocking the beverage line based on a predetermined change in the electrical parameter measured by the sensor, the predetermined change in value being indicative of bubbles in the beverage.

2. The connector according to claim 1 wherein the sensor is a capacitive sensor for measuring capacitance/changes in capacitance of the beverage in the connector conduit.

3. The connector according to claim 1 wherein the sensor comprises a downstream electrode spaced and electrically insulated from an upstream electrode by an insulating spacer.

4. The connector according to claim 3 wherein the sensor is adapted to apply an input voltage and/or current to one of the upstream/downstream electrodes.

5. The connector according to claim 4 wherein the input voltage and/or current is an alternating input voltage and/or current.

6. The connector according to claim 5 wherein the sensor further comprises a measuring transducer for detecting a resultant electrical signal in the other upstream/downstream electrode to that to which the input current and/or voltage is applied.

7. The connector according to claim 6 wherein sensor is adapted to apply an input voltage and/or current to the downstream electrode and the measuring transducer is connected to the upstream electrode.

8. The connector according to claim 6 wherein the measuring transducer is provided on a PCB, the PCB being mounted within the connector or within a housing on an outside surface of the connector.

9. The connector according to claim 3 wherein the electrodes extend into or partly define the connector conduit.

10. The connector according to claim 9 wherein the upstream electrode comprises an upstream probe and the downstream electrode comprises a downstream probe, each probe extending from the insulating spacer into the connector conduit.

11. The connector according to claim 10 comprising a substantially L-shaped body defining an L-shaped connector conduit wherein the sensor is located at or around an elbow of the L-shaped connector conduit.

12. The connector according to claim 11, wherein one of the upstream or downstream probes extends substantially axially within a first branch of the L-shaped connector conduit, and the other one of the upstream or downstream probes extends perpendicularly across a second branch of the L-shaped connector conduit such that the two probes are parallel.

13. The connector according to claim 12, wherein the upstream probe extends substantially axially within an upstream branch of the L-shaped connector conduit, and the downstream probe extends perpendicularly across a downstream branch of the L-shaped connector conduit such that the two probes are parallel.

14. The connector according to claim 12, wherein the downstream probe extends substantially axially within a downstream branch of the L-shaped connector conduit, and the upstream probe extends perpendicularly across an upstream branch of the L-shaped connector conduit such that the two probes are parallel.

15. The connector according to claim 3 wherein the upstream and downstream electrodes are spaced from one another by the insulating spacer by at least 8 mm.

16. The connector according to claim 15 comprising a substantially L-shaped body or a substantially tubular body.

17. The connector according to claim 1 comprising a connector cooling circuit comprising a connector cooling line and a connector cooling return line for carrying chilled cooling medium, the cooling lines being in heat exchange relationship with the connector conduit or a cooling channel for carrying chilled cooling medium, the cooling channel surrounding the connector conduit.

18. A bubble detection system for use in a beverage dispense system, the bubble detection system comprising a connector according to claim 1 and a valve operable to close the beverage line upon receipt of the output signal from the electrical sensor.

19. A beverage dispense system comprising a beverage line connectable to a beverage supply for transporting beverage from the beverage supply to a dispensing site and a bubble detection system according to claim 18, wherein the connector is connected to a distal end of the beverage line that is distal from the dispensing site.

20. A beverage dispense system comprising a beverage line connectable to a beverage supply for transporting beverage from the beverage supply to a dispensing site and a connector according to claim 1, wherein the connector is connected to a distal end of the beverage line.

\* \* \* \* \*